United States Patent
Inoue et al.

(10) Patent No.: US 8,147,064 B2
(45) Date of Patent: Apr. 3, 2012

(54) FUNDUS CAMERA

(75) Inventors: Hiroyuki Inoue, Kawasaki (JP); Shinya Tanaka, Katowice (PL); Hiroshi Aoki, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 32 days.

(21) Appl. No.: 12/870,506

(22) Filed: Aug. 27, 2010

(65) Prior Publication Data

US 2011/0051087 A1    Mar. 3, 2011

(30) Foreign Application Priority Data

Sep. 1, 2009   (JP) .................. 2009-201291

(51) Int. Cl.
 *A61B 3/14* (2006.01)
 *A61B 3/10* (2006.01)
(52) U.S. Cl. .................. 351/206; 351/208; 351/221
(58) Field of Classification Search ........... 351/200–246
 See application file for complete search history.

(56) References Cited

U.S. PATENT DOCUMENTS

| 6,755,526 | B2 * | 6/2004 | Shibata ................ 351/206 |
| 7,641,340 | B2 * | 1/2010 | Ichikawa ............. 351/208 |
| 7,651,223 | B2 * | 1/2010 | Ichikawa ............. 351/208 |
| 7,980,696 | B1 * | 7/2011 | Taki et al. ........... 351/206 |
| 2010/0187410 | A1 | 7/2010 | Iijima |

FOREIGN PATENT DOCUMENTS

| JP | 1-178237 A | 7/1989 |
| JP | 5-95907 A | 4/1993 |
| JP | 8-275921 A | 10/1996 |

\* cited by examiner

*Primary Examiner* — Mohammed Hasan
(74) *Attorney, Agent, or Firm* — Canon U.S.A., Inc., IP Division

(57) ABSTRACT

When pattern recognition of a fundus image is started in step S1, output from a fundus image sensing unit is compared with a regional pattern of stored fundus image specific regions in step S2, and it is decided whether to proceed to pattern recognition. If pattern recognition is possible, based on an AF evaluation value, the lens is driven, with which automatic focusing is completed.

13 Claims, 11 Drawing Sheets

FUNDUS CAMERA

BACKGROUND OF THE INVENTION

1. Field of the Invention

The present invention relates to a fundus camera to take an image of a fundus of a subject's eye for use, for example, in ophthalmic hospitals and mass medical examination.

2. Description of the Related Art

It is well known that to facilitate focusing on a fundus of a subject's eye, images of indexes are projected to the fundus, and a positional relation of index images is observed through a focusing lens of an observing and photographing system, to thereby obtain a clear image of the fundus.

Japanese Patent Application Laid-Open No. 5-95907 discusses a fundus camera, in which two focus split index images projected onto the fundus are captured and a focus state is detected based on positions of the focus split index images while attenuating the brightness of the index images.

Japanese Patent Application Laid-Open No. 8-275921 discusses an ophthalmic apparatus, in which focus index images are projected onto the fundus, the focus index images are captured by a photographing optical system, and a focus state is detected.

Japanese Patent Application Laid-Open No. 1-178237 discloses a modified embodiment of an apparatus for automatic focusing (AF) by capturing an electronic image during observation and detecting contrast between captured images. In other words, when first and second ranges are brought into focus by using high frequency components of fundus images to perform focusing, and a distance in a light axis direction is obtained from the focusing lens positions.

However, a conventional fundus camera divides incident light into a fundus illumination light flux, a focus split index light flux, and an observation photographing light flux in regions near the pupil of the examined eye in order to remove reflected light from the cornea. Therefore, when there are personal differences in aberration in the examined eye's optical system, if an image is captured only based on the focus split index image positions which are predetermined, there is a possibility that errors may occur in focusing for some examined eyes, resulting in a blurred fundus image.

As a solution to this problem, an apparatus is known, in which electronic image sensing is performed even during observation, and automatic focusing (AF) is carried out by detecting contrast among captured images.

In an apparatus as described above, the drawback that a focusing error may occur for some examined eyes, which will result in an out-of-focus image can be solved. However, because regions where a focus is detected are fixed in some portions of the imaging system, there is another problem yet to be solved.

In a conventional method of AF detection, in which, as to some regions of the fundus, fundus images are formed at different distances in the depth direction; therefore, the focus detection ranges have to be fixed, it is necessary to guide the line of sight of the examined eye in such a manner that the regions to be focused may match a focus detection range.

Like general AF single-lens reflex cameras, even if the focus detection range is movable, it must still be moved manually, and further the AF detection position changes with the movement of the eyeball.

SUMMARY OF THE INVENTION

The present invention is directed to providing a fundus camera capable of easy alignment.

According to an aspect of the present invention, a fundus camera includes a fundus illuminating optical system configured to illuminate a fundus of a subject's eye, a fundus photographing optical system including a focusing lens driven to bring the fundus into focus, a focusing lens drive unit configured to drive the focusing lens, a fundus image capturing unit arranged in a conjugate relationship with the fundus in the fundus photographing optical system, a display monitor configured to display a fundus image captured by the fundus image capturing unit, a focus state detecting unit configured to detect an AF evaluation value representing a degree of a focus state based on an output signal from the fundus image capturing unit, and a lens drive control unit configured to drive the focusing lens based on the AF evaluation value detected by the focus state detecting unit. The focus state detecting unit includes a fundus position detecting unit configured to detect a specific region of the fundus image by using a regional pattern inherent in a fundus region based on output from the fundus image capturing unit, and a focus detection range determining unit configured to determine a focus detection range based on output of the fundus position detecting unit. Furthermore, the focus state detecting unit calculates the AF evaluation value in the focus detection range determined by the focus detection range determining unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
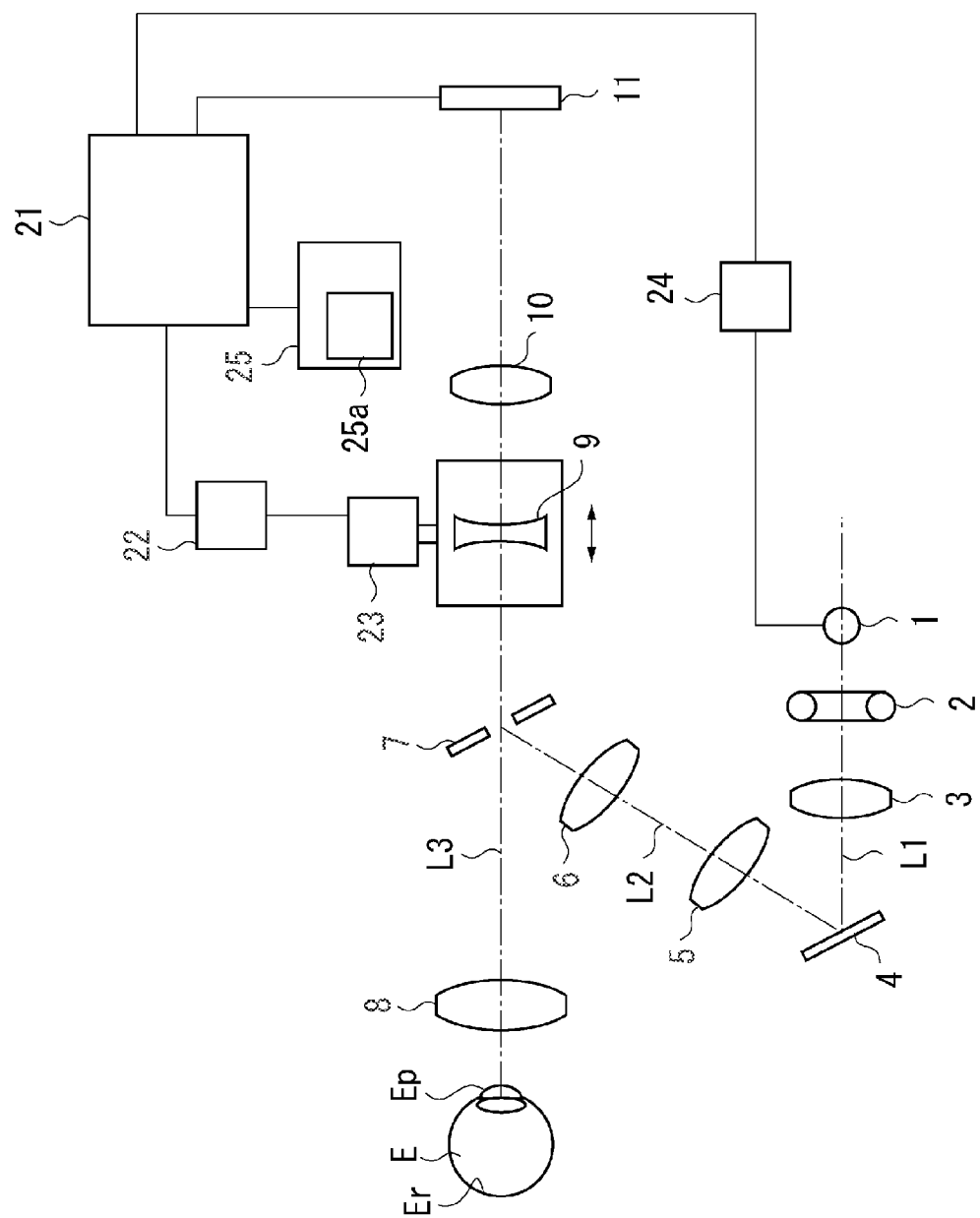
FIG. 1 is a block diagram of a fundus camera according to a first exemplary embodiment of the present invention.

A first exemplary embodiment of the present invention will be described. FIG. 1 is a block diagram of a fundus camera. In a fundus illumination optical system, an observation light source 1, a photographic light source 2, a lens 3, and a mirror 4 are arranged on a light axis L1, and also relay lenses 5, 6, and a pierced mirror 7 with a hole in the center are arranged on a light axis L2 in a reflection direction of the mirror 4 in series. Furthermore, an objective lens 8 is arranged facing the examined eye E on a light axis L3 in a reflection direction of the mirror 7. The observation light source 1 for illuminating the fundus comprises, for example, a halogen lamp that emits a stationary light, and the photographic light source 2 comprises, for example, a stroboscopic tube that emits visible light.

On the other hand, a fundus photographing optical system is formed by successively arranging, behind a pierced mirror 7 on the light axis L3, a focusing lens 9 configured to adjust a focus by moving the focusing lens 9 along a light axis, a photographic lens 10, and a fundus image sensing unit 11 placed at a position in a conjugate relation with the fundus Er.

Output of a fundus image sensing unit 11 is coupled to a focus state detecting unit 21. Output of the focus state detecting unit 21 is coupled to a focusing lens 9 via a lens drive control unit 22 and a focusing lens drive unit 23, and further coupled through an illuminating light quantity control unit 24 to an observation light source 1 and to a display monitor 25. The display monitor 25 is provided with a focus detection range display 25a.

While observing a fundus image on the display monitor 25, and using the observation light source 1, the examiner fine-tunes positioning of the examined eye E relative to a housing provided with the optical system, then adjusts the focus, and captures an image with the photographic light source.

The present exemplary embodiment provides an AF function to automatically adjust the focus. A focus detection range is shown to the examiner, on a window in a focus detection range display 25a, which is superposed onto a fundus image captured by a fundus image sensing unit 11. Because the focus detection range is presented to the examiner in a visual form, the AF operability is improved.

In a fundus camera configured as described, a focus is detected by detecting contrast of a fundus image formed by a photographing light flux. Therefore, in contrast to a conventional apparatus which projects a focus index through a front eye region outside of the photographing light flux, this fundus camera can perform automatic focusing not based on chromatic aberration of the examined eye optical system.

Figure 2:
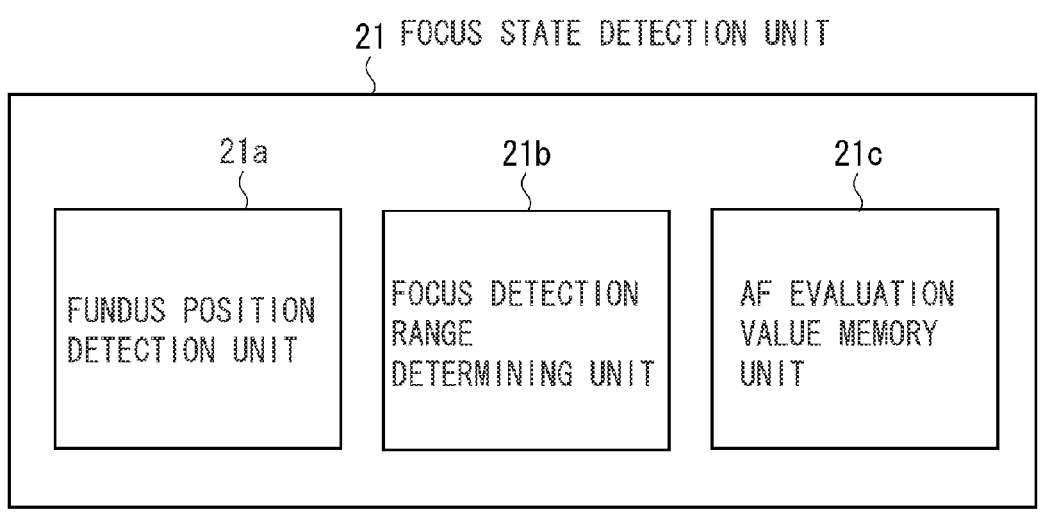
FIG. 2 is a structure diagram of a focus state detecting unit.

As illustrated in FIG. 2, the focus state detecting unit 21 includes a fundus position detecting unit 21a configured to detect a specific position of the fundus Er, and a focus detection range determining unit 21b configured to determine a focus detection range based on a signal from the fundus position detecting unit 21a. The focus state detecting unit 21 further includes an AF evaluation value memory unit 21c configured to store an AF evaluation value and a position of the focusing lens 9 when an AF evaluation value is detected.

Figure 3:
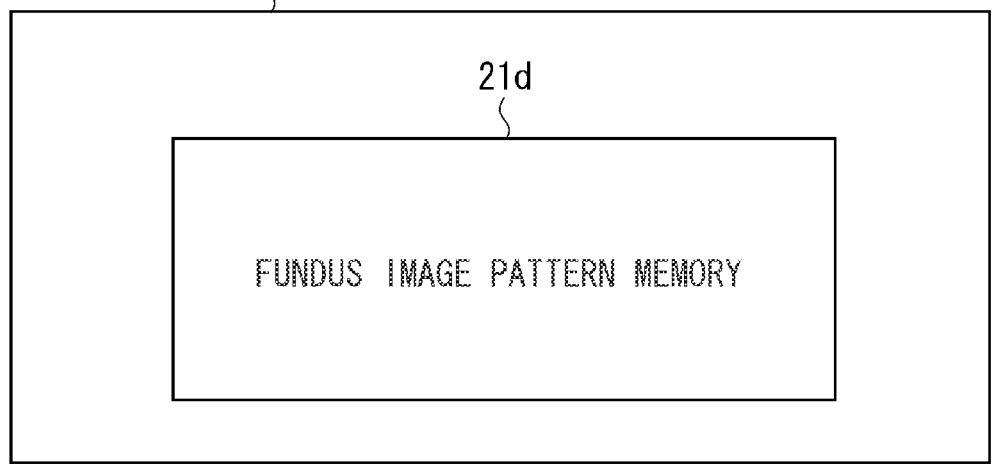
FIG. 3 is a structure diagram of a fundus position detecting unit.
Figure 4:
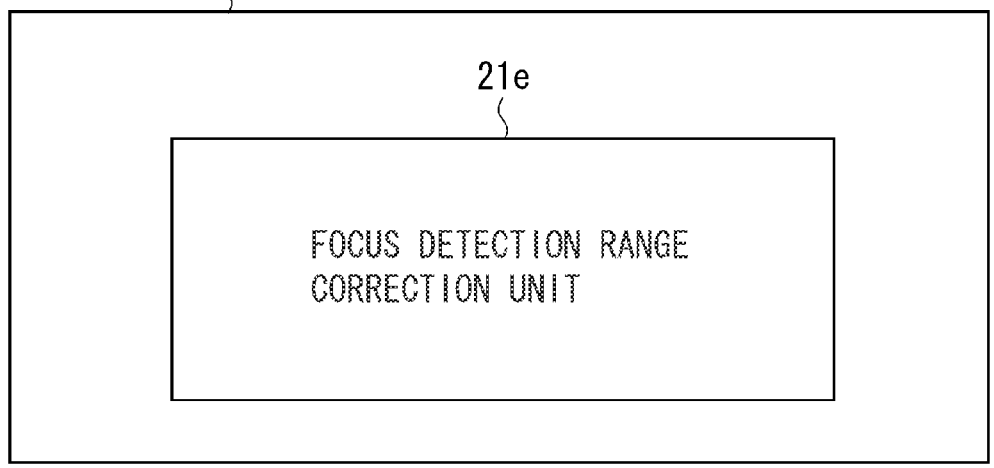
FIG. 4 is a structure diagram of a focus detection range determining unit.

As illustrated in FIG. 3, the fundus position detecting unit 21a also includes a fundus image pattern memory 21d to store a fundus image pattern as a regional pattern based on a standard image of a specific region in a fundus image. This fundus image pattern is used to extract a specific region from the fundus image. Positional information about a specific region is obtained by pattern matching between regional patterns stored in the fundus image pattern memory 21d and an output signal from the fundus image sensing unit 11. The focus detection range determining unit 21b determines a range where a focus is to be adjusted based on output of fundus image's specific region extracted by the fundus position detecting unit 21a. However, as illustrated in FIG. 4, to enable the examiner to correct the size of the focus detection range, the focus detection range determining unit 21b preferably includes a focus detection range correcting unit 21e configured to correct the range by performing a cursor operation on the image of the display monitor 25.

The focus state detecting unit 21 calculates an AF evaluation value of a focus detection range determined by the focus detection range determining unit 21b, and also stores information about the position of the focusing lens 9 at this time.

Figure 5:
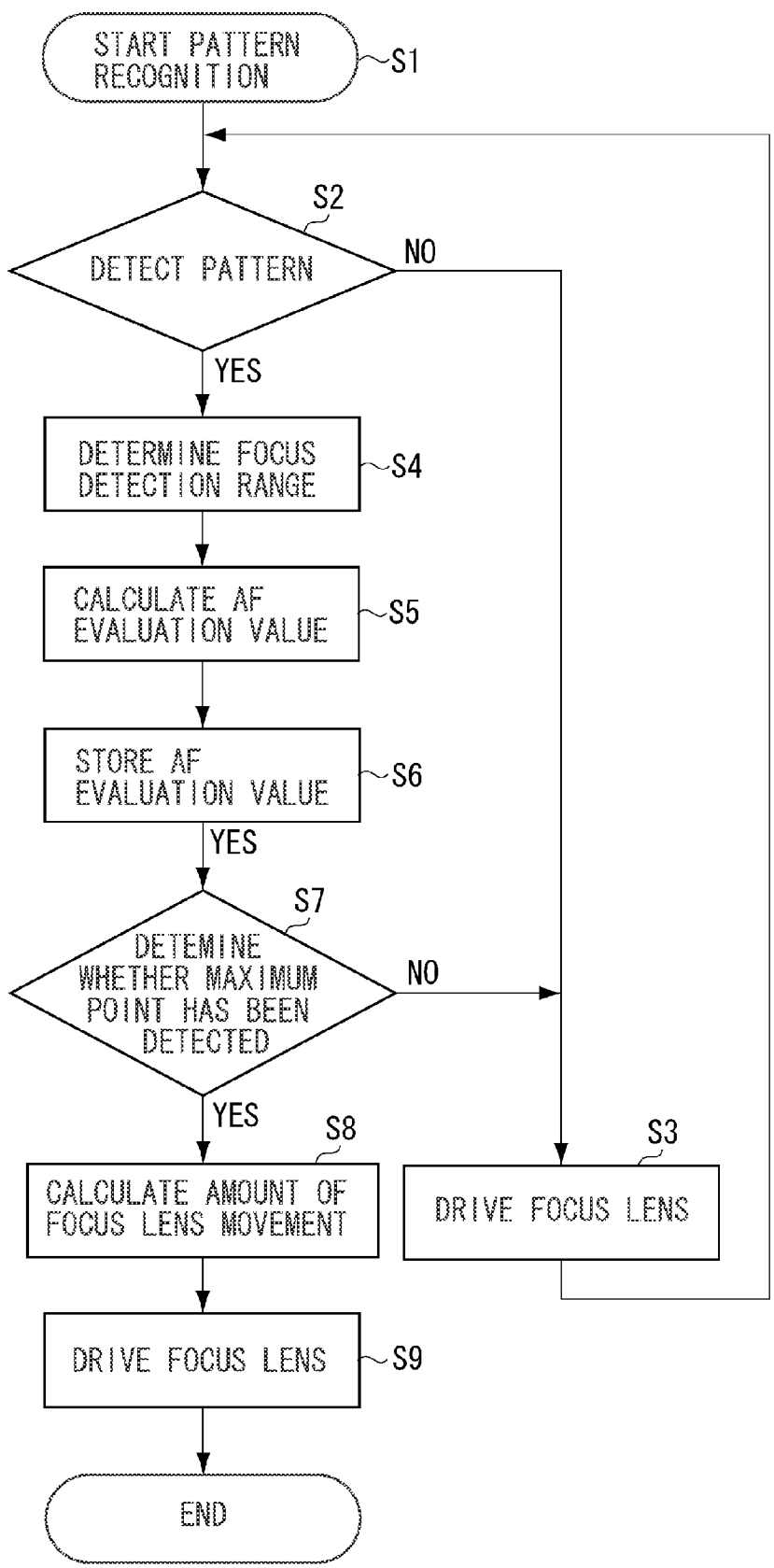
FIG. 5 is a flowchart of a method for controlling the fundus camera.

FIG. 5 is a flowchart of an AF control method. When an instruction to start AF operation is issued by an AF start switch (not illustrated), in step S1, a recognition process of a fundus image pattern is started. In step S2, the fundus position detecting unit 21a calculates, for example, a correlation function between output of the fundus image sensing unit 11 and a regional pattern of a fundus image's specific region stored in the fundus image pattern memory 21d. It is determined whether a range has a correlation value equal to or larger than a threshold value and can be used as a focus detection range. Then, it is determined whether pattern recognition can be performed in this focus detection range.

When automatic focusing is started, if the focusing lens 9 is displaced widely from a position at a focusing time and pattern recognition is disabled, the processing proceeds to step S3, where pattern recognition is performed repeatedly by driving the focusing lens 9 little by little until pattern recognition becomes possible.

In step S2, if it is determined that pattern recognition is possible, in step S4, the focus detection range determining unit 21b determines a focus detection range based on output of the fundus position detecting unit 21a. When a focus detection range is determined, in step S5, the focus state detecting unit 21 calculates an AF evaluation value representing a degree of focus state in the focus detection range. A method for calculating an AF evaluation value will be described later, and calculated AF evaluation values are stored in the AF evaluation value memory unit 21c.

Figure 6:
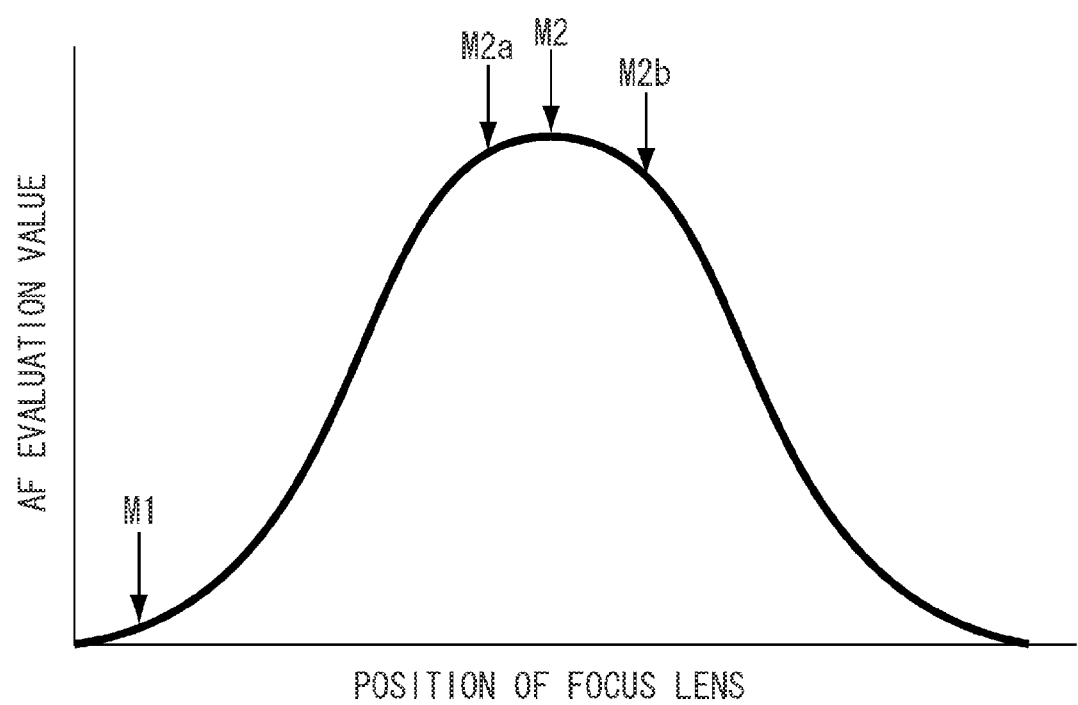
FIG. 6 is a diagram illustrating a principle of contrast detection.

FIG. 6 is a diagram illustrating a principle of focus detection by contrast detection. This focus detection system utilizes a fact that particular high frequency components of brightness signal becomes maximum when an image is in focus, and the focus state detecting unit detects and uses high frequency components of an input luminance signal as an AF evaluation value. A horizontal axis indicates the position of the focusing lens 9, and a vertical axis indicates the level of AF evaluation value. At in-focus position M2, the AF evaluation value is at a maximum, and at position M1 where the image is widely out of focus, the AF evaluation value is small. In this exemplary embodiment, by utilizing this principle of contrast detection, focus correction suitable for the aberration of a human eye optical system is performed.

In step S7, by using the above-described principle of contrast detection, it is detected whether a maximum point at position M2 illustrated in FIG. 6 is included in AF evaluation values stored in step S6. If a decision at step S7 is made for the first time, a maximum point cannot be determined, accordingly the processing proceeds to step S3, where the focusing lens 9 is driven.

In step S7, if a maximum point is detected among the AF evaluation values, in step S8, the focus state detecting unit 21 calculates an amount of movement of the focusing lens 9. The amount of movement of the focusing lens 9 in step S8 denotes a drive amount of the focusing lens 9 up to a detection position of a maximum point M2 of the AF evaluation value. On the basis of the drive amount of the focusing lens 9 calculated in step S8, the lens drive control unit 22 in step S9 sends a signal to the focus lens drive unit 23 to drive the focusing lens 9, with which automatic focusing is finished.

As described above, automatic focusing is completed by driving the focusing lens 9 in step S9 based on the driven amount of the focusing lens 9 calculated in step 8. However, after step S9, steps S2 to S5 may be performed to obtain an AF evaluation value. When this AF evaluation value is compared with the AF evaluation value in which a maximum point has been determined for the first time, if a difference between the two AF values is lower than a threshold value, automatic focusing may be completed.

On the other hand, if a maximum point is not detected in the AF evaluation value in step S7, the processing proceeds to step S3 and the focusing lens drive unit 23 drives the focusing lens for a predetermined distance. Then, again in step S2, pattern recognition is performed, and in step S4, a focus detection range is determined. As described above, even if the examined eye E is displaced during automatic focusing, the focus detection range can follow the movement of the examined eye E. If pattern recognition or maximum point detection in the AF evaluation value is unsuccessful after a predetermined number of trials, the processing may be stopped considering that an error has occurred.

Figure 7:
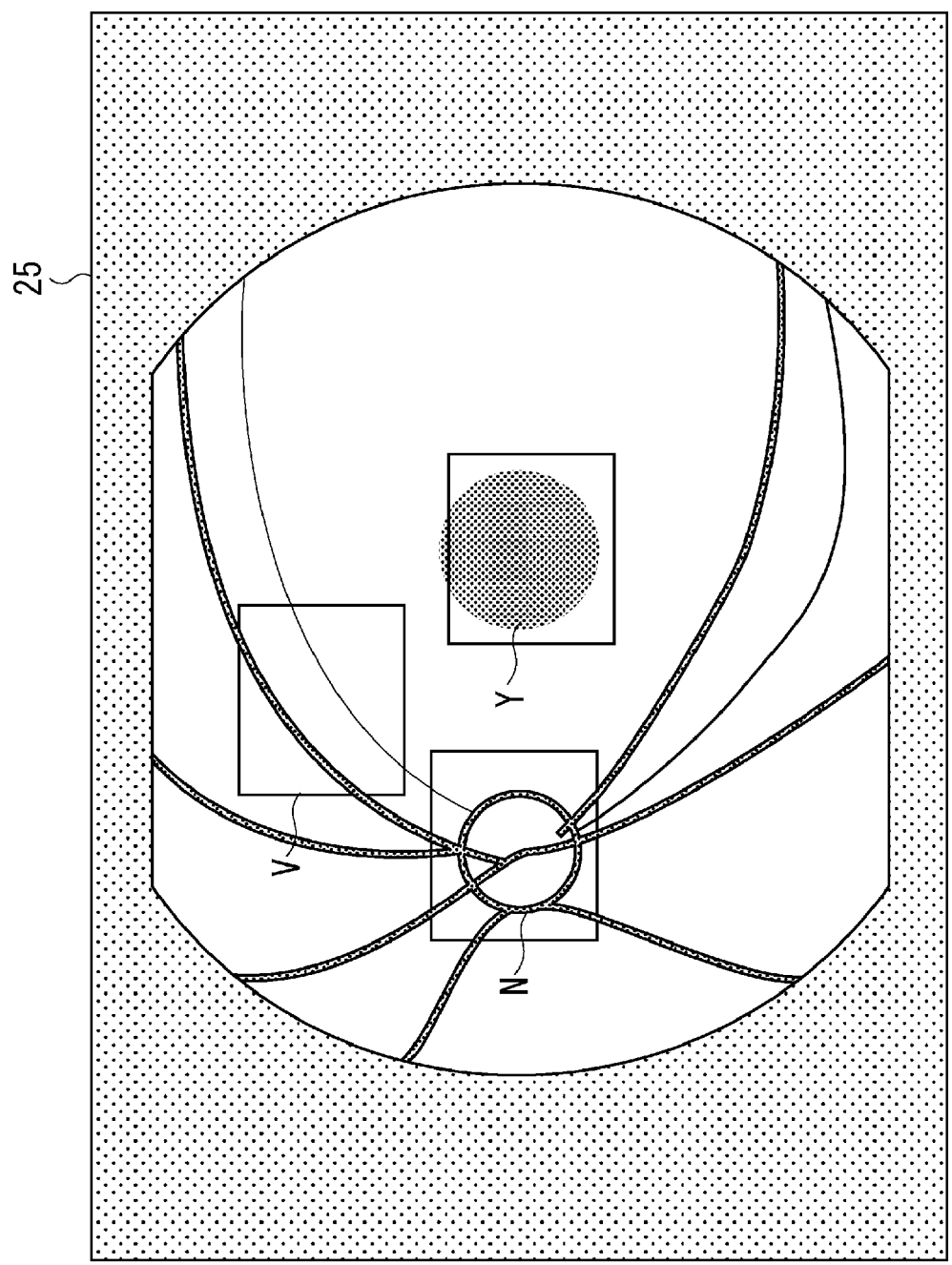
FIG. 7 is a diagram illustrating a fundus image displayed on a display monitor.

FIG. 7 is a diagram illustrating a fundus image displayed on the display monitor 25, in which a positional relation does not widely change among a papilla portion N, a medium and large blood vessel portion V, and a yellow spot portion Y inherent in the fundus region, though there are personal differences. Generally, the above-mentioned positional relation of the left eye and the right eye is mirror-reversed.

Figure 8:
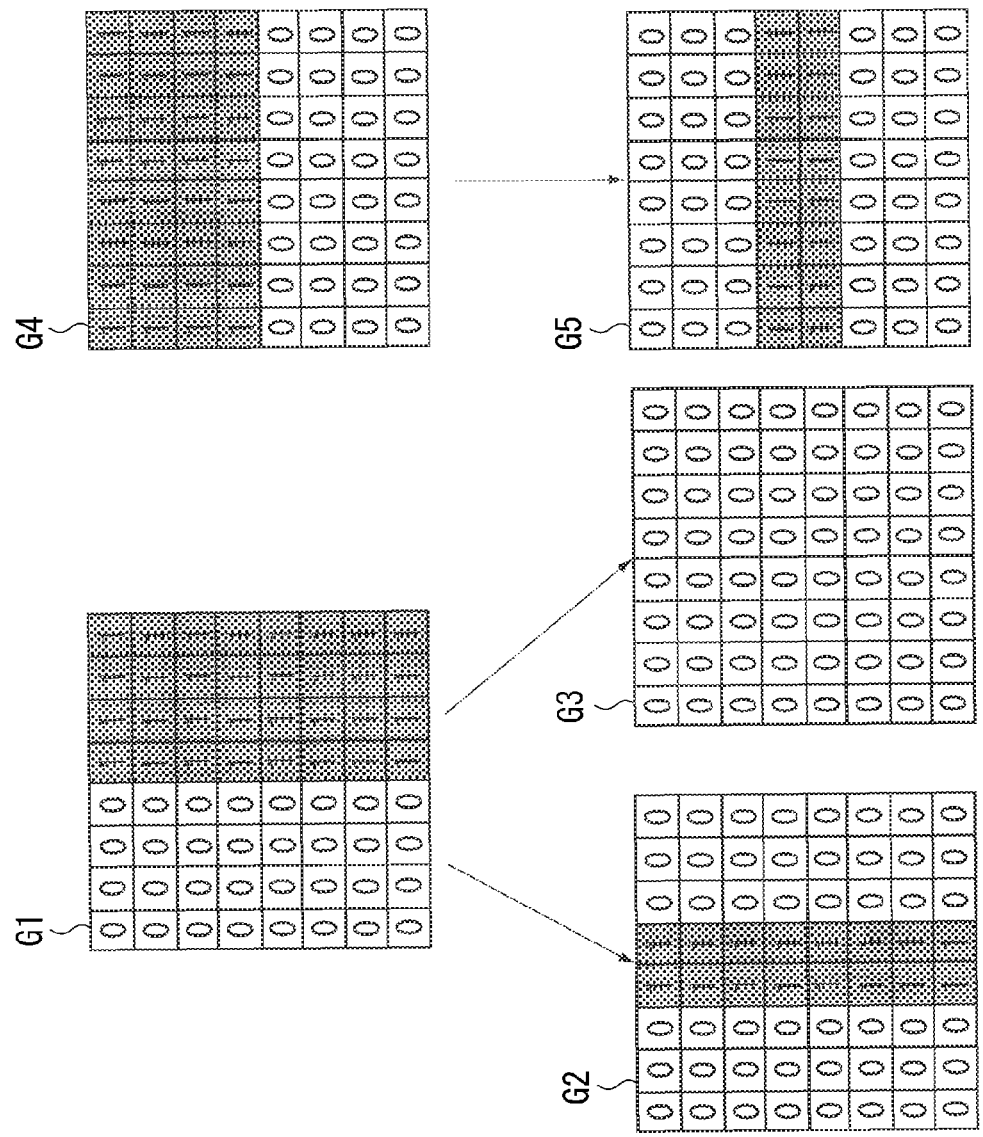
FIG. 8 is a diagram illustrating a method for calculating AF evaluation values.

FIG. 8 is a diagram illustrating an AF evaluation value when the focus detection range is a regional pattern of the medium and large blood vessel portion V. As a method for easily detecting high frequency components from an image, an AF evaluation value is calculated, in which when luminance signals are compared between a target pixel and 8 adjacent pixels on left and right, up and down, and on diagonal sides of the target pixel, a largest difference value is taken as an AF evaluation value of the target pixel. An image G1 is an example of a clipped piece of an image when the medium and large blood vessel portion V extends in a vertical direction, in which the pixels have luminance signals "0" or "1".

When this focus detection method is applied to the image, AF evaluation values are given with respect to the pixels as illustrated in an image G2. A total of AF evaluation values of the pixels can be taken as an AF evaluation value of an entire image.

To calculate easily and at a high speed an AF evaluation value, it is possible to adopt a method in which by comparing luminance signals between a target pixel and two adjacent pixels, if there is no difference, an AF evaluation value is "0" or if there is a difference, an AF evaluation value is "1". According to this method, since the number of pixels to be compared is smaller than in the preceding method, load on calculation can be reduced. However, if the luminance signals between a target pixel and two vertically adjacent pixels are compared, an image G3 is output, in which edges of the medium and large blood vessel portion V as a target cannot be detected.

On the other hand, if this method is applied to an image G4 in which the medium and large blood vessel portion V extends in the horizontal direction, an image is output as illustrated in an image G5, and results can be obtained similar to the image G2 which includes AF evaluation values calculated by the preceding method. In other words, while if a detection method utilizing directional dependence described above is selected, arithmetic operation time can be reduced, images to be used need to be appropriately selected.

As described above, in the images G1 and G4, differences in luminance are compared between each pixel and adjacent pixels, and expressed in bit maps as illustrated in the images G2 and G5 respectively. A larger difference between adjacent pixel values means a larger difference in luminance between the adjacent pixels.

The medium and large blood vessel portion V discussed in an example of the present exemplary embodiment runs in an arc form roughly around the yellow spot Y on the fundus Er. A blood vessel portion, which forms a thick blood trunk, is located near the papilla portion N. Therefore, since the edges of the medium and large blood vessel portion V are located in a direction of ±45°, if a detection method is adopted which enables selection of that direction, low-load high-speed automatic focusing can be achieved without sacrificing the sensitivity of AF evaluation value.

While the medium and large blood vessel portion V on the fundus Er was used for pattern recognition of a fundus image according to the present embodiment, other portions, such as regional patterns of the papilla portion N and the yellow spot portion may be stored in the fundus image pattern memory 21d and automatic focusing can also be performed on those regions.

As described above, by automatically determining a focus detection range by pattern recognition, the operability of automatic focusing can be improved. Since the focus detection position can follow the movement of the examined eye E, focusing accuracy can be improved.

Since the focus state detecting unit 21 refers to a luminance value of each pixel when calculating an AF evaluation value, it may be detected whether the luminance value of the determined focus detection range has saturated. If saturation has occurred, the focus state detection unit 21 sends a signal to the illumination light quantity control unit 24 to control a light quantity of the observation light source 1, which enables automatic focusing with high accuracy. When contrast detection is to be performed on the papilla portion N where "whitening" is likely to occur, for example, by adjusting the light quantity of the illumination optical system, a fundus image with high accuracy and diagnostic value can be obtained.

In the first exemplary embodiment, pattern recognition is performed on a specific region on the fundus Er. In the second exemplary embodiment, before automatic focusing is started, the examiner selects a region of the fundus Er where a focus detection range is to be set and a focus detection range is determined based on this selection to perform automatic focusing.

In the second exemplary embodiment, the fundus pattern memory 21d contains a plurality of fundus image patterns, including regional patterns, such as the papilla portion N, the yellow portion Y, and the medium and large blood vessel portion V. The examiner preliminarily selects a region to be focused on based on a subject's case by using a region selecting device, such as a cursor on the display monitor 25. This operation corresponds to selecting one of a plurality of fundus image patterns in the fundus position detecting unit 21a. The examiner 1 detects a position of a selected fundus image pattern based on output of the fundus image sensing unit 11, and notifies a selected position to the focus detection range determining unit 21b. This operation and a subsequent operation are similar to those in the first exemplary embodiment.

The examiner 1 is here supposed to select one fundus region, but may select a plurality of regions. In this case, AF evaluation values are calculated for the plurality of regions, and only a total of those values may be used as an overall evaluation value. By detecting a maximum value of an overall evaluation value, an evenly focused image can be obtained, which covers a plurality of regions selected by the examiner. By this method, a focused fundus image can be captured in a region of interest for the examiner, so that a fundus image with high diagnostic value can be provided.

As described above, by recognizing a pattern of a region which the examiner wants to look at in diagnosis, and determining a focus detection range, a fundus image high in diagnostic value can be obtained. In the papilla portion N, the medium and large blood vessel portion V, an yellow spot portion Y, where a relatively large number of high frequency components are included in an image, a proper focus detection range can be determined, and contrast detection can be performed with high accuracy.

Contrast detection can be performed with high accuracy by chiefly detecting the medium and large blood vessel portion V where there are little personal differences, but not the papilla portion N where personal differences tend to be highly irregular. In addition, because the running direction of the medium and large blood vessels V can be identified easily, by detecting the contrast in a direction orthogonal to the medium and large blood vessel portion V, high-speed low-cost contrast detection can be performed with high accuracy and less calculation load.

The examiner selects a focus detection range from among a plurality of fundus regions so that images having high diagnostic value and representing pathological changes which the examiner wants to investigate can be obtained.

In a second exemplary embodiment, the examiner selects a focus detection range before automatic focusing is started. In a third exemplary embodiment, the examiner selects a focus detection range from among specific regions obtained by pattern recognition processing, and performs automatic focusing.

Like the second exemplary embodiment, in the third exemplary embodiment, the fundus image pattern memory contains a plurality of fundus image patterns, including regional patterns of the papilla portion N, the yellow spot portion Y, and the medium and large blood vessel portion V. In a third exemplary embodiment, differences from the first and second embodiments are that positions of plural fundus image patterns are detected based on output of the fundus image sensing unit 11, and that information about those positions is delivered to the focus detection range determining unit 21b.

Figure 9:
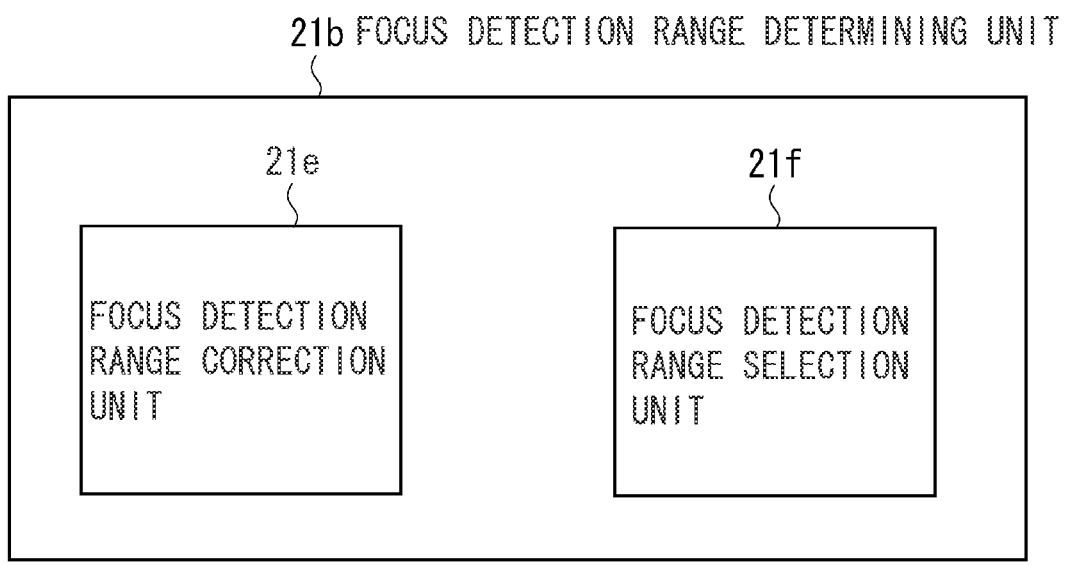
FIG. 9 is a structure diagram of a focus detection range determining unit according to a third exemplary embodiment of the present invention.

In the third exemplary embodiment, the focus detection range determining unit 21b includes a focus detection range correcting unit 21e and a focus detection range selecting unit 21f as illustrated in FIG. 9. The focus detection range display unit 25a on the display monitor 25 supplies the examiner with a plurality of specific regions of a fundus image extracted by the fundus position detecting unit 21a. Using a cursor as the focus detection range selecting unit 21f, the examiner selects one region, for which a focus detection range is to be set, from among the supplied specific regions. The specific region of a fundus image may be supplied to the examiner when a predetermined number of pattern recognition have been detected or when the focusing lens 9 has moved an entire movable range.

The examiner corrects a size of the focus detection range with the focus detection range correcting unit 21e. Thus, the examiner can manually correct the position and the size of the focus detection range, and can capture a fundus image focusing correctly on a region the examiner wants to observe.

While the examiner selects one fundus region in the third embodiment, like in the second embodiment, it is possible for the examiner to select a plurality of regions. Supply of information about the specific regions of the selected fundus image and subsequent operations are similar to the first embodiment.

In the second and third embodiments, AF evaluation values are calculated for one or more focus detection ranges selected by the examiner from among a plurality of fundus image regions obtained by pattern recognition processing. In a fourth embodiment, however, AF evaluation values are calculated for all regions of a plurality of fundus images obtained by pattern recognition, and an evaluation about the maximum values and then, automatic focusing are performed.

In the fourth embodiment, the focus state detecting unit 21 calculates AF evaluation values for a plurality of fundus image specific regions of a fundus image extracted by the fundus position detecting unit 21a. The focus state detecting unit 21 can obtain images focused evenly at a plurality of regions extracted by pattern recognition by using a total value of the AF evaluation values as an overall evaluation value, and by detecting a maximum value of the overall evaluation value.

Figure 10:
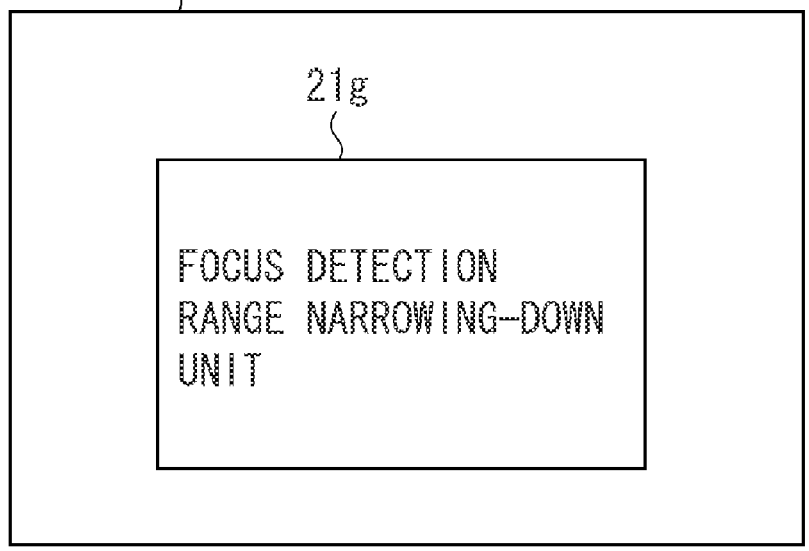
FIG. 10 is a structure diagram of a focus detection range determining unit according to a third exemplary embodiment of the present invention.

In the fourth embodiment, as illustrated in FIG. 10, the focus detection range determining unit 21b includes a focus detection range limiting unit 21g. The focus detection range limiting unit 21g automatically determines, as a focus detection range, one region with a highest AF evaluation value from among the specific regions of the fundus image extracted by the fundus position detecting unit 21a, and sends the focus detection range to the focus state detecting unit 21. The selected specific region of the fundus image is sent to the focus detection range determining unit 21b, and subsequent operations are performed similar to the preceding embodiments. Thus, a fundus image in sharp focus can be captured automatically, and a fundus camera with excellent AF operability can be provided.

Because a focus detection range can be determined automatically, the AF performance can be improved.

In the first to fourth embodiments, positions of specific regions of the fundus image are detected only by pattern recognition by the fundus position detecting unit 21a. In a fifth embodiment, by combining pattern recognition of the papilla portion N and left-eye/right-eye detection, the medium and large blood vessel portion V including specific high frequency components is detected and automatic focusing is performed.

Figure 11:
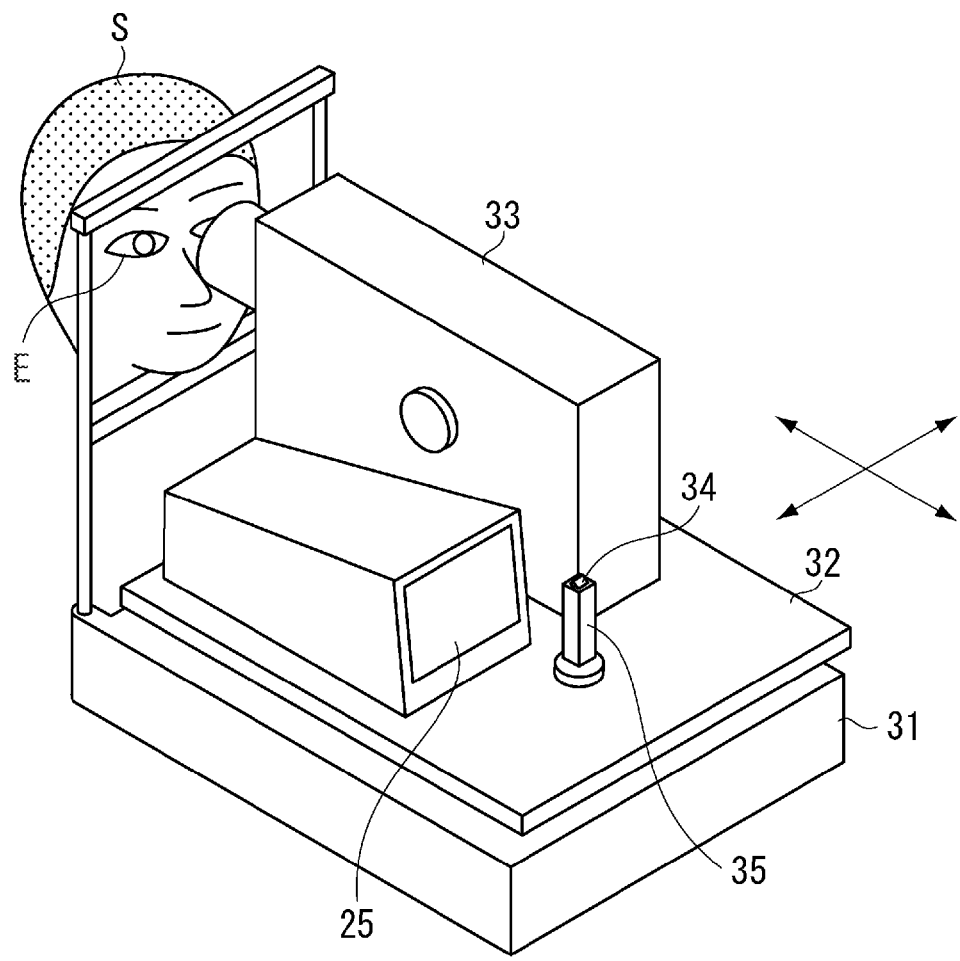
FIG. 11 is an external view of the fundus camera.

FIG. 11 is an external view of a fundus camera according to a fifth embodiment, in which a table 32, movable in the back-forth and left-right directions as indicated by arrows, is mounted on a pedestal 31. A housing 33 containing an optical system of a fundus camera illustrated in FIG. 1, a display monitor 25, and an operation bar 35 fitted with a shooting button 34 are mounted on the table 25.

The examiner operates the operation bar 35, and adjusts the table 32 in the left/right direction on a horizontal plane to match the left and right eyes of a subject. Since a left/right eye detecting unit 36 is disposed between the pedestal 31 and the table 32, the left-right position of the housing 33 can be detected, so that it is known which of the subject's examined eyes E is being observed and photographed.

Figure 12:
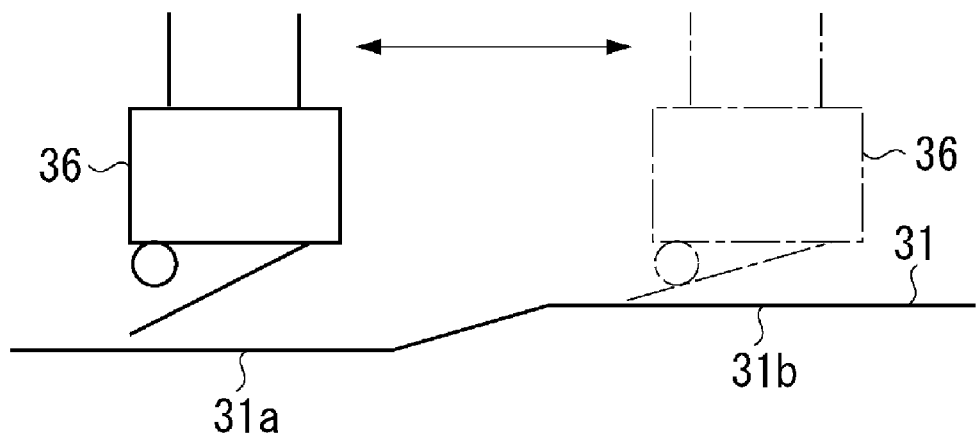
FIG. 12 is a structure diagram of a left/right eye detecting unit.

FIG. 12 is a diagram illustrating a detection method by the left/right eye detecting unit 36. A low portion 31a and a high portion 31b, showing a height difference, are formed on the upper surface of the pedestal 31. The left/right eye detecting unit 36 is made of a micro switch and provided on a bottom surface of the table 32. The left/right eye detecting unit 36 turns on, for example, when it comes above the low portion 31a of the pedestal 31, and turns off, when it comes on the high portion 31b of the pedestal 31. In other words, by positioning the low portion 31a on the left side and the high portion 31b on the right side, the on/off state of the left/right eye detecting unit 36 can be detected, and the tested eye, left or right, facing the housing 33 can be detected.

A method will be described by which to detect a focus detection range, above all, the medium and large blood vessel portion V illustrated in FIG. 7 the left eye or right eye is detected by the left/right eye detecting unit 36 and pattern recognition of the papilla portion N is performed by the fundus position detecting unit 21a.

When a specific region is detected on a fundus Er and it can be determined which of a subject's eyes is being observed, it is possible to predict a structure of the fundus Er. Therefore, the medium and large blood vessel portion V can be detected by detecting the left eye or right eye with the L-R eye detecting unit 36 and by pattern recognition of the papilla portion N. A detected medium and large blood vessel portion V is sent to the focus detection range determining unit 21b and a subsequent operation are performed similar to the preceding embodiments.

In the fifth embodiment, only the papilla portion N that allows easy pattern recognition is detected, and based on this detection, other regions on the fundus Er are determined as a focus detection range. Accordingly, there is a possibility that a specific region on the fundus Er deviates from the focus detection range due to personal differences. Therefore, a focus detection range correcting unit 21e is provided to enable the examiner to manually correct the position and the size of the focus detection range, so that a sharply focused fundus image can be obtained of a region the examiner wants to investigate.

By identifying the medium and large blood vessel portion V or the yellow spot portion Y using efficient pattern recognition of the papilla region N and adopting the left/right eye detecting unit, a focus detection range can be determined more accurately. Therefore, calculation load is reduced, calculation time is shortened, and high-speed automatic focusing can be realized.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-201291 filed Sep. 1, 2009, which is hereby incorporated by reference herein in its entirety.

What is claimed is:

1. A fundus camera comprising:
a fundus illuminating optical system configured to illuminate a fundus of a subject's eye;
a fundus photographing optical system including a focusing lens driven to bring the fundus into focus;
a focusing lens drive unit configured to drive the focusing lens;
a fundus image capturing unit arranged in a conjugate relationship with the fundus in the fundus photographing optical system;
a display monitor configured to display a fundus image captured by the fundus image capturing unit;
a focus state detecting unit configured to detect an AF evaluation value representing a degree of a focus state based on an output signal from the fundus image capturing unit; and
a lens drive control unit configured to drive the focusing lens based on the AF evaluation value detected by the focus state detecting unit,
wherein the focus state detecting unit includes a fundus position detecting unit configured to detect a specific region of the fundus image by using a regional pattern inherent in a fundus region based on output from the fundus image capturing unit, and a focus detection range determining unit configured to determine a focus detection range based on output of the fundus position detecting unit, and the focus state detecting unit calculates the AF evaluation value in the focus detection range determined by the focus detection range determining unit.

2. The fundus camera according to claim 1, wherein the display monitor includes a focus detection range display unit configured to display the focus detection range determined by the focus detection range determining unit overlapped with the fundus image obtained by the fundus image capturing.

3. The fundus camera according to claim 1, wherein in the regional pattern a nipple portion of the fundus is identified.

4. The fundus camera according to claim 1, wherein in the regional pattern medium and large blood vessels of the fundus are identified.

5. The fundus camera according to claim 1, wherein in the regional pattern a yellow spot of the fundus is identified.

6. The fundus camera according to claim 1, wherein the fundus position detecting unit includes a plurality of the regional patterns.

7. The fundus camera according to claim 6, wherein the focus detection range determining unit includes a region selecting unit to allow an examiner to previously select a plurality of the regional pattern.

8. The fundus camera according to claim 6, wherein the focus detection range determining unit includes a focus detection range selecting unit configured to display a plurality of the focus detection ranges identified based on a plurality of the regional patterns, and allow an examiner to select one or more of focus detection ranges from the displayed ranges.

9. The fundus camera according to claim 1, wherein the focus lens is driven based on the AF evaluation values for a plurality of focus detection ranges identified according to a plurality of the regional patterns.

10. The fundus camera according to claim 9, wherein the focus detection range determining unit includes a focus detection range refining unit configured to determine one focus detection range out of a plurality of the focus detection ranges based on the AF evaluation values according to a plurality of the focus detection ranges.

11. The fundus camera according claim 1, further comprising a left/right eye detecting unit configured to determine whether a left eye or a right eye is being observed, based on a position of a table on which an optical system is mounted, wherein positions of medium and large blood vessels or a position of a yellow spot are detected based on a position of a papilla area detected by the fundus position detecting unit and on output of the left/right-eye detecting unit.

12. The fundus camera according to claim 1, wherein the focus detection range determining unit further includes a focus detection range correcting unit configured to correct the positions and sizes of the focus detection ranges.

13. The fundus camera according to claim 1, further comprising an illumination light quantity control unit configured to adjust an illumination light quantity of an observation light source by the fundus illumination optical system, wherein the illumination light quantity control unit controls the illumination light quantity based on output of the focus state detecting unit.

* * * * *